(12) United States Patent
Michel et al.

(10) Patent No.: US 9,175,279 B1
(45) Date of Patent: Nov. 3, 2015

(54) METHOD OF PURIFYING FACTOR VII AND/OR FACTOR VIIA

(71) Applicant: CSL Limited, Parkville, Victoria (AU)

(72) Inventors: Angela Anita Yvonne Michel, Bern (CH); Ian Walker, Malvern East (AU); Duy Dinh Nguyen, Kingsbury (AU)

(73) Assignee: CSL Limited, Parkville, Victoria (AU)

( * ) Notice: Subject to any disclaimer, the term of this patent is extended or adjusted under 35 U.S.C. 154(b) by 0 days.

(21) Appl. No.: 14/205,877

(22) Filed: Mar. 12, 2014

Related U.S. Application Data

(60) Provisional application No. 61/794,904, filed on Mar. 15, 2013.

(51) Int. Cl.
*C12N 9/64* (2006.01)
*A61K 38/48* (2006.01)

(52) U.S. Cl.
CPC .......... *C12N 9/6437* (2013.01); *A61K 38/4846* (2013.01)

(58) Field of Classification Search
IPC ....................................................... C12N 9/6437
See application file for complete search history.

(56) References Cited

U.S. PATENT DOCUMENTS

| | | |
|---|---|---|
| 2004/0063187 A1 | 4/2004 | Roemisch et al. |
| 2009/0047723 A1 | 2/2009 | Jensen et al. |

FOREIGN PATENT DOCUMENTS

| | | |
|---|---|---|
| WO | WO 01/38228 A1 | 5/2001 |
| WO | WO 2005/111225 A1 | 11/2005 |
| WO | WO 2007/090584 A1 | 8/2007 |

OTHER PUBLICATIONS

Jesty et al., "Purification of Factor VII from bovine plasma," J Biol Chem 249(2):509-515, 1974.*
G.A. Allen et al., "A Variant of Recombinant Factor VIIa With Enhanced Procoagulant and Antifibrinolytic Activities in an In Vitro Model of Hemophilia," *Arterioscler. Thromb. Vacs. Biol.*, 27: 683-689 (2007).
E. Persson, "Variants of Recombinant Factor VIIa With Increased Intrinsic Activity," *Semin. Hematol*, 41(Suppl. 1): 89-92 (2004).

* cited by examiner

*Primary Examiner* — Rosanne Kosson
(74) *Attorney, Agent, or Firm* — Finnegan, Henderson, Farabow, Garrett & Dunner, LLP

(57) ABSTRACT

The present invention relates generally to a method of purifying Factor VII and/or Factor VIIa from a solution containing either or both proteins, the method comprising: diluting the solution containing Factor VII and/or Factor VIIa in a loading buffer; adding the diluted solution from step (i) to a multi-modal anion exchange resin under conditions selected such that Factor VII and/or Factor VIIa is bound to the resin; optionally washing the resin with a wash buffer; adding an elution buffer to the resin under conditions selected such that Factor VII and/or Factor VIIa is eluted from the resin; and recovering the eluted recombinant Factor VII and/or Factor VIIa; wherein the loading buffer, the optional wash buffer and the elution buffer each comprise about 35 mM or less of calcium ions.

18 Claims, 8 Drawing Sheets
(1 of 8 Drawing Sheet(s) Filed in Color)

FIGURE 6

Capto Adhere and rVIIa-FP

| Column Operation Mode | | Step | Recovery (%) | | | RP-HPLC (%) | | | SE-HPLC (%) | | | PS80 | |
|---|---|---|---|---|---|---|---|---|---|---|---|---|---|
| | | | Chromogenic | Staclot | Protein# | VIIa | VII | SP | Aggregate | Monomer | Fragment | (%) | mg/L |
| "pseudo" FT | DEV | Load | 3 | 3 | | 84.9 | 10.0 | 5.1 | 3.2 | 95.3 | 1.6 | 0.0775 | 775 |
| | | FT | 3 | 3 | 15 | 47.4 | 45.9 | 6.7 | 42.4 | 31.6 | 33.0 | ND | ND |
| | | Eluate | 75 | 72 | 63 | 88.9 | 6.2 | 4.9 | 2.2 | 97.2 | 0.7 | 0.0009 | 9 |
| | | Strip | 9 | 6 | 12 | 71.4 | 20.7 | 7.8 | 3.1 | 95.8 | 1.0 | ND | ND |
| | Eng5A | Load | 4 | 4 | 6 | 86.2 | 9.5 | 4.4 | 5.1 | 93.4 | 1.5 | 0.104 | 1040 |
| | | FT | 0.02 | 0.04 | 10 | ND | ND | ND | ND | ND | ND | 0.061 | 610 |
| | | Eluate | 78 | 72 | 67 | 87.7 | 8.2 | 4.1 | 3.3 | 95.7 | 1.0 | 0.0008 | 8 |
| | | Strip | 6 | 5 | 8 | 72.6 | 19.9 | 7.5 | 11.6 | 85.4 | 3.0 | ND | ND |
| Bind and Elute | New Method | Load | | | | 85.6 | 10.1 | 4.3 | 6.4 | 91.5 | 2.1 | 0.0763 | 763 |
| | | FT | 0.02 | 0.04 | 10 | ND | ND | ND | 60.3 | 35.1 | 4.6 | 0.0747 | 747 |
| | | Eluate | 95 | 73 | 80 | 85.7 | 10.2 | 4.2 | 0.7 | 97.5 | 1.8 | 0.0014 | 14 |
| | | Strip | 5 | 5 | 9 | 72.8 | 18.9 | 8.3 | 18.1 | 80.5 | 1.5 | 0.0003 | 3 |

NOTE: Protein content determined by UV is difficult to measure in the FT (flow-through) as PS80 also absorbs at the required wavelengths.

METHOD OF PURIFYING FACTOR VII AND/OR FACTOR VIIA

This application claims priority to U.S. Provisional Application No. 61/794,904, filed Mar. 15, 2013, which is incorporated herein by reference.

TECHNICAL FIELD

The present invention relates generally to a method of purifying Factor VII and/or Factor VIIa from a solution containing said protein. More specifically, the present invention relates to a method of purifying a solution containing Factor VII and/or Factor VIIa by mixed-mode (multi-modal) anion exchange chromatography The present invention also relates generally to solutions and pharmaceutical formulations comprising the Factor VII and/or Factor VIIa recovered by such methods, and uses thereof.

BACKGROUND

Factor VII is an important protein in the blood coagulation cascade. It is a vitamin K-dependent plasma protein that is synthesized in the liver and secreted into the blood as a single-chain glycoprotein, with a molecular weight of around 53 kDa. Synthesised as a zymogen, Factor VII is then converted into its activated form (FVIIa) by proteolytic cleavage at a single site, R152-I153, resulting in two chains linked by a single disulfide bridge. Recombinant human FVIIa is used for the treatment of bleeding episodes, e.g. in hemophilia or trauma and conditions associated with Factor VII/Factor VIIa deficiencies.

Purification of Factor VII (rFVII) or activated Factor VII (rFVIIa) is generally carried out using a combination of ion exchange and immuno-affinity chromatography that uses a calcium-dependant anti-FVII monoclonal antibody. Although this immuno-affinity based purification step is highly selective and provides protein of high purity, there are disadvantages. For example, the antibodies can potential leach into the final therapeutic product, which may affect the safety of the final composition. The cost of producing the monoclonal antibody (mAb) immuno-affinity matrix is considerably greater as compared to more conventional, non-antibody based purification matrices.

While replacement of the immuno-affinity step with a different purification technique would be advantageous, this would require removal of non-Factor VII-related contaminants, as well as the ability to separate any unwanted isoforms of Factor VII that may be present in the culture supernatants, such as aggregates. Examples of non-Factor VII-related cont74aminants include blood-borne products such as prothrombin, plasminogen, tissue plasminogen activator (tPA) and other proteases (e.g., where Factor VII is being purified from a blood product such as plasma) or it may include material derived from cell culture such as cell debris and cell culture media (e.g., where the Factor VII is recombinantly produced). The level of contaminants can adversely affect the final preparation and thus limit its use, particularly for human applications.

Other methods for the purification of Factor VII have been described. For example, US 20040063187 is directed to a method of purifying the proenzyme form of Factor VII using anion-exchange chromatography (Mono Q Sepharose resin). The solution containing the proenzyme form of Factor VII was added to the resin using a buffer solution of 20 mM Na acetate, 0.1 M glycine, pH 4.5. The fraction passing through was discarded and the bound proteins were eluted using 20 mM Na acetate, 2 M NaCl, pH 4.5. The eluate was diluted in a buffer of 5 mM Na citrate, 50 mM NaCl, pH 6.0.

US 20090047723 is directed to a method for purifying Factor VII (rFVII) or activated Factor VII (rFVIIa) by subjecting the proteins to liquid chromatography on a hydroxyapatite (HAP) column. A solution containing Factor VII was added to a hydroxyapatite column in 25 mM imidazole, approx. 6 mM NaCl, approx. 18 mM $CaCl_2$, pH 6.5. The bound protein was washed first in 25 mM imidazole, pH 6.5, then using 100 mM Na-Phosphate, pH 6.3, followed by 150 mM Na-Phosphate, 1 M NaCl to elute contaminants and unwanted Factor VII isoforms. Factor VII protein was then eluted using Na-Phosphate, 1 M NaCl, with a Na-Phosphate concentration gradient of from 150 mM to 500 mM together with a pH gradient of from 6.3 to 8.0.

The present invention provides an improved method of purifying Factor VII and/or Factor VIIa from a solution containing either or both proteins by using mixed-mode (multi-modal) anion exchange chromatography. Whilst the method can be used to remove any non-Factor VII-related contaminant from the solution, it is particularly useful for removing solvent and/or detergent from the solution that has been introduced, for example, during a virus inactivation step.

SUMMARY OF THE INVENTION

In an aspect of the present invention, there is provided a method of purifying Factor VII and/or Factor VIIa from a solution containing either or both proteins, the method comprising:
  (i) diluting the solution containing Factor VII and/or Factor VIIa in a loading buffer;
  (ii) adding the diluted solution from step (i) to a multi-modal anion exchange resin under conditions selected such that Factor VII and/or Factor VIIa is bound to the resin;
  (iii) optionally washing the resin with a wash buffer;
  (iv) adding an elution buffer to the resin under conditions selected such that Factor VII and/or Factor VIIa is eluted from the resin; and
  (v) recovering the eluted Factor VII and/or Factor VIIa;
wherein the loading buffer, the optional wash buffer and the elution buffer each comprise about 35 mM or less of calcium ions.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 6 shows data derived from the two different purification processes, as outlined in FIG. 6; namely, two separate control runs using 20 mM Ca$^{2+}$ in the Equilibration/Load/PLW/Elution buffers ("DEV" and "EngSA") and a test run using 5 mM Ca$^{2+}$ in the Equilibration/Load buffer, no Ca$^{2+}$ in the PLW buffer and 20 mM Ca$^{2+}$ in the Elution buffer ("New Method"). % recovery was determined by chromogenic, Staclot and UV absorption (Protein*). The amount of Factor VIIa, Factor VII (non-activated) and side product (SP) that is formed by degradation of Factor VIIa were determined by Reversed phase-HPLC. The level of Factor VII aggregates, monomers and fragments were determined by size exclusion-HPLC. The presence of PS80 was also measured and represented as % (v/v) and mg/L.

DETAILED DESCRIPTION

Figure 1:
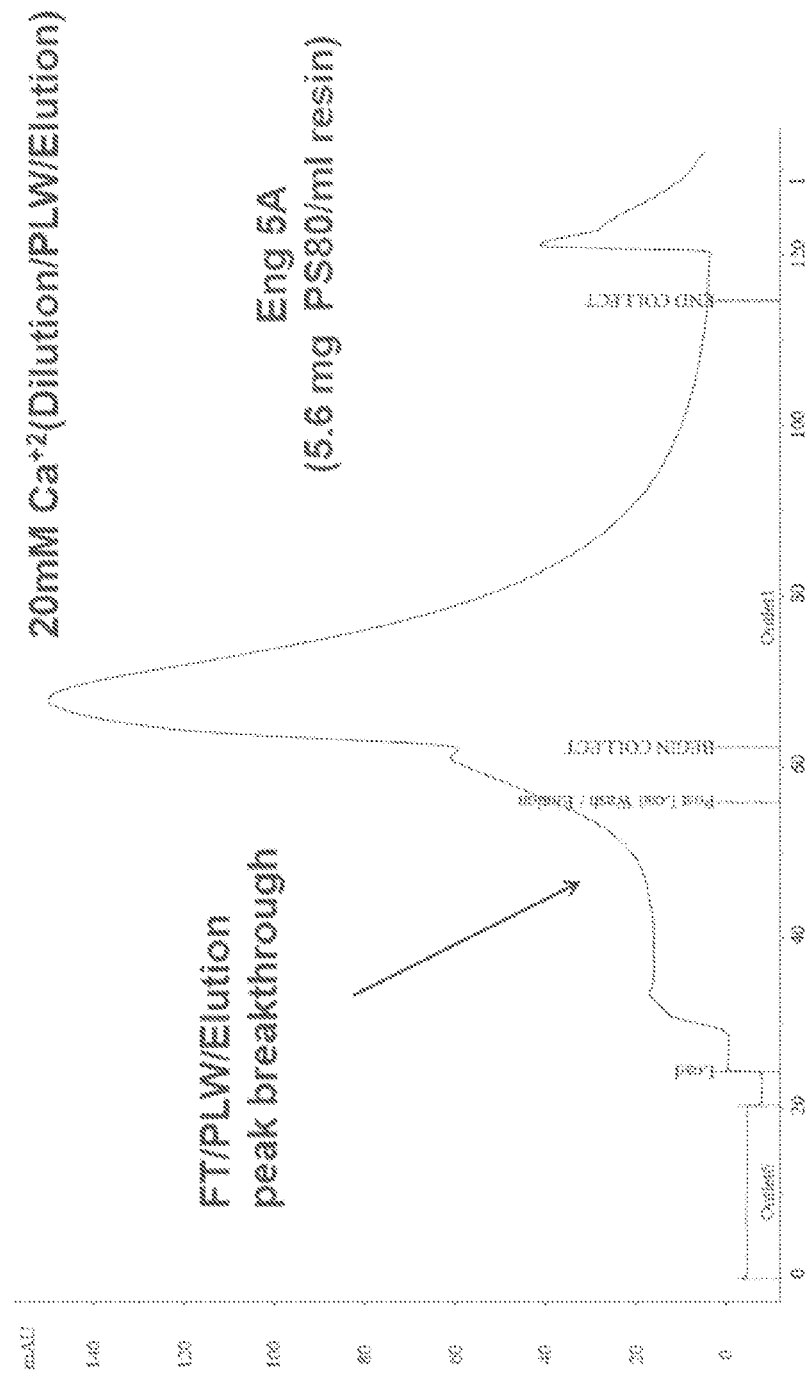
FIG. 1 shows an example of the Capto™ Adhere chromatogram designated Eng 5A. Load and Equilibration/PLW/Elution buffer containing 20 mM $CaCl_2$.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It must be noted that, as used in the subject specification, the singular forms "a", "an" and "the" include plural aspects unless the context clearly dictates otherwise. Thus, for example, reference to "a formulation" includes a single formulation, as well as two or more formulations.

In the absence of any indication to the contrary, reference made to a "%" content throughout this specification is to be taken as meaning % w/w (weight/weight). For example, a solution comprising at least 80% total protein of Factor VII and/or Factor VIIa is taken to mean a solution comprising Factor VII and/or Factor VIIa at a concentration of at least 80% w/w of total protein. This can be calculated by any means known to persons skilled in the art, for example, by dividing the amount of Factor VII and/or Factor VIIa derived from the clottable protein assay (e.g., Staclot) by the total protein amount derived from a standard protein assay (e.g. Biuret) and multiplying by 100. Other methods of measuring Factor VII and/or Factor VIIa include high pressure liquid chromatography (HPLC), such as reversed phase (RP)-HPLC or size exclusion (SE)-HPLC, chromogenic methods and by UV absorbance.

Factor VII and/or Factor FVIIa as used in the present invention encompasses variants and fragments of Factor VII and/or Factor VIIa as for example described in WO 2005/111225, including chemical conjugates as for example disclosed in WO 2007/022512 as well fusion proteins of Factor VII and/or Factor VIIa as for example disclosed in WO 2007/090584. Factor VII and/or Factor VIIa can be both of plasmatic or recombinant origin. Also contemplated herein are recombinant variants of Factor VII, such as those described by Allen et al. (Arteriosclerosis, Thrombosis, and Vascular Biology. 2007; 27: 683-689) and Persson et al. (Semin. Hematol. 2004; 41(1, Suppl.1):89-92).

The present invention is predicated, at least in part, on the finding that passing a solution comprising Factor VII and/or Factor VIIa through a mixed-mode (multimodal) anion exchange chromatographic resin and recovering the solution comprising Factor VII and/or Factor VIIa that passes through the resin is an efficient alternative to existing purification processes for reducing the level of contaminants in the solution.

The inventors have found that at higher calcium levels the purification can be performed in a "pseudo flow-through" mode in which Factor VII and/or Factor VIIa is binding to the column, but in which Factor VII and/or Factor VIIa can be displaced and eluted already in the washing buffer. In these embodiments a washing step is optional, or the wash buffer may the same buffer as the elution buffer.

Thus, in an aspect of the present invention, there is provided a method of purifying Factor VII and/or Factor VIIa from a solution containing either or both proteins, the method comprising:
 (i) diluting the solution containing Factor VII and/or Factor VIIa in a loading buffer;
 (ii) adding the diluted solution from step (i) to a multimodal anion exchange resin under conditions selected such that Factor VII and/or Factor VIIa is bound to the resin;
 (iii) optionally washing the resin with a wash buffer;
 (iv) adding an elution buffer to the resin under conditions selected such that Factor VII and/or Factor VIIa is eluted from the resin; and
 (v) recovering the eluted Factor VII and/or Factor VIIa;
wherein the loading buffer, the optional wash buffer and the elution buffer each comprise about 35 mM or less of calcium ions.

It has been further found by the inventors, that by further decreasing the calcium concentration in the wash buffer the Factor VII and/or Factor VIIa remains bound to the resin during the washing step and is only eluted from the resin when an elution buffer is applied comprising higher calcium concentration.

In another aspect of the present invention, there is provided a method of purifying Factor VII and/or Factor VIIa from a solution containing either or both proteins, the method comprising:
 (i) diluting the solution containing Factor VII and/or Factor VIIa in a loading buffer;
 (ii) adding the diluted solution from step (i) to a multimodal anion exchange resin under conditions selected such that Factor VII and/or Factor VIIa is bound to the resin;

(iii) washing the resin with a wash buffer under conditions selected such that Factor VII and/or Factor VIIa remains bound to the resin;

(iv) adding an elution buffer to the resin under conditions selected such that Factor VII and/or Factor VIIa is eluted from the resin; and (v) recovering the eluted Factor VII and/or Factor VIIa;

wherein the loading buffer and/or the wash buffer each comprise about 35 mM or less of calcium ions.

Solutions containing Factor VII and/or Factor VIIa would be known to persons skilled in the art. Examples include conditioned media derived from culturing cells that produce either or both of the recombinant protein(s) or solutions derived from initial purification steps (e.g., an initial purification step through an ion exchange resin).

Persons skilled in the art will understand that the starting solution may contain no Factor VIIa (activated Factor VII), but that the activated form may be formed in situ (e,g, during the purification steps herein described). Thus, the starting solution may contain only Factor VII (non-activated) but the purified (end-) product may contain recombinant Factor VII and (activated) Factor VIIa.

Chromatographic processes typically employ a solid support, also referred to interchangeably herein as a resin. Suitable solid supports would be familiar to persons skilled in the art. Examples include inorganic carriers, such as glass and silica gel, organic, synthetic or naturally occurring carriers, such as agarose, cellulose, dextran, polyamide, polyacrylamides, vinyl copolymers of bifunctional acrylates, and various hydroxylated monomers, and the like. Commercially available carriers are sold under the names of Sephadex™, Sepharose™, Hypercel™, Capto™, Fractogeff, Macro-Prep™, Unosphere™, GigaCap™, Trisacryl™, Ultrogel™, Dynospheres™, Macrosorb™ and XAD™ resins.

The chromatography steps will generally be carried out under non-denaturing conditions and at convenient temperatures in the range of about +10° C. to +30° C., more usually at about ambient temperatures. The chromatographic steps may be performed batch-wise or continuously, as convenient. Any convenient method of separation may be employed, such as column, centrifugation, filtration, decanting, or the like.

Chromatography can be performed using any means known to persons skilled in the art. For example, the chromatography steps according to the present invention can use axial flow columns, such as those available from GE Healthcare, Pall Corporation and Bio-Rad, or radial flow columns, such as those available from Proxcys. The chromatography steps according to the present invention can also be conducted using expanded bed technologies.

Multimodal (or mixed-mode) protein chromatography is a technique that is based on solid supports that have been functionalized with ligands capable of multiple modes of interaction: ion exchange, hydroxyapatite, affinity, size exclusion, and hydrophobic interactions. The ability to combine these separation methods can enhance selectivity in a protein purification process. However, unlike affinity chromatography, where a specific site on the protein is targeted, mixed-mode chromatography employs ligands that have no known specificity for the target protein(s). Mixed-mode resins effectively combine complementary chromatography methods within a single resin and can therefore reduce the total number of column steps needed in a purification process. Because these mixed-mode elements are present in a single resin, it contributes to affinity-like binding and selectivity.

Binding and elution of the target protein of interest are controlled and optimized by the parameters relevant to each mode; for example, salt concentration for hydrophobic interactions and ionic strength for ionic interactions.

There are a number of commercially available mixed-mode media combining different chromatographic elements, such as hydroxyapatite and hydrophobic ion exchange ligands.

Hydroxyapatite is a form of calcium phosphate that comprises sets of five calcium doublets (C-sites) and pairs of hydroxide residues containing phosphate triplets (P-sites) arranged in a repeating geometric pattern. Hydroxyapatite chromatography has been applied to the purification of monoclonal and polyclonal antibodies, antibody fragments, recombinant proteins, viral particles and DNA.

By contrast, hydrophobic ion exchange resins (also referred to herein as multimodal or mixed-mode ion exchange resins) incorporate hydrophobic and ionic elements. For ion exchange binding and elution, conditions such as salt, pH, ionic strength are optimised to enable the binding of the target protein of interest to the ligands and the subsequent elution of the bound target protein from the ligands. For hydrophobic interactions, conditions such as salt type and concentration are optimised. Due to the dependency of these interactions, buffer conditions must be optimized for binding, washing, and elution for optimal purification.

Multi-modal ion exchange resins include multi-modal anion exchange resins comprising any suitable multi-modal anion exchange ligand. Multi-modal anion exchange resins are solid supports that comprise a multi-modal anion exchange ligand which, in addition to comprising a charged group, also comprises at least one other functionality, such as a hydrophobic group capable of interacting with a target molecule by hydrogen bonding, hydrophobic, and van der Waals interactions or the like. Multi-modal anion exchange ligands are typically non-specific, in that they are capable of binding two or more different classes of proteins.

Multi-modal anion exchange resins differ from multi-modal cation exchange resins with hydrophobic binding, which contain a secondary amine and is cationic over a wide pH range, therefore, it behaves as both a hydrophobic interaction resin and an anionic exchange media.

Suitable ligands that can be used with multi-modal anion exchange resins will be known to persons skilled in the art. Examples include ligands comprising amine or other positively charged groups. Functional amines can be selected from the group consisting of primary, secondary and tertiary and quaternary amines; hydrazine, such as mono-substituted hydrazine and di-substituted hydrazine; poly-amines; poly-imines; poly-Q (where Q refers to quaternary ammonium groups); aniline; and hydroxylamines. In an embodiment, the multi-modal anion exchange ligand is N-benzyl-N-methyl ethanolamine, such as that used in Capto™ Adhere (GE Life Sciences). Other examples of suitable multi-modal anion exchange ligands are described in WO 2001/38228.

Multi-modal anion exchange ligands also include ligands whose positive charge can be induced by varying buffer conditions, such as pH. Such ligands are often used in hydrophobic charge induction chromatography (HCIC). Suitable charge induction anion exchange ligands that can be used as multi-modal anion exchange ligands are known to persons skilled in the art. Examples include mercaptoethylpyridine (4-mercaptoethylpyridine, e.g., MEP Hypercel), n-hexylamine (e.g., HEA Hypercel) and phenylpropylamine (e.g., PPA Hypercel). With MEP, for example, the pyridine ring is uncharged at neutral and basic pH, however, as the pH decreases, the pyridine nitrogen becomes positively charged, turning the resin into a mixed-mode anion exchange resin.

Suitable loading (which may also be referred to herein as a dilution), wash and elution buffers would be known to persons skilled in the art. An example includes buffers comprising 2-(N-morpholino)ethanesulfonic acid (MES) and NaCl. The pH of the buffer may vary, but in preferred embodiments, the loading buffer has a pH of 6.0. In another embodiment, the loading buffer comprises 20 mM 2-(N-morpholino)ethanesulfonic acid (MES) and 200 mM NaCl, pH 6.0.

The present inventors have found that adjusting the amount of $Ca^{2+}$ ions in the buffers to 35 mM or less can result in improved protein recovery from the multi-modal anion exchange column, whilst also reducing the amount of aggregated Factor VII and/or Factor VIIa in the recovered product. The amount of $Ca^{2+}$ in any one or more of the buffers can be 35 mM, 34 mM, 33 mM, 32 mM, 31 mM, 30 mM, 29 mM, 28 mM, 27 mM, 26 mM, 25 mM, 24 mM, 23 mM, 22 mM, 21 mM, 20 mM, 19 mM, 18 mM, 17 mM, 16 mM, 15 mM, 14 mM, 13 mM, 12 mM, 11 mM, 10 mM, 9 mM, 8 mM, 7 mM, 6 mM, 5 mM, 4 mM, 3 mM, 2 mM or 1 mM. In an embodiment, the loading buffer, the wash buffer and the elution buffer each comprise about 20 mM or less of calcium ions. In another embodiment, the loading buffer, the wash buffer and the elution buffer each comprise about 20 mM calcium ions. Suitable sources of calcium ions would be known to persons skilled in the art. An examples is calcium chloride ($CaCl_2$).

In an embodiment, the loading buffer, the wash buffer and the elution buffer each comprise the same amount of calcium ions. In another embodiment, the constituents of the loading buffer, wash buffer and elution buffer are the same. In a preferred embodiment, the buffers comprise 20 mM 2-(N-morpholino)ethanesulfonic acid (MES), 20 mM $CaCl_2$ and 200 mM NaCl, pH 6.0.

During chromatographic purification, the resin is usually equilibrated with an equilibration buffer. In preferred embodiments, the equilibration buffer is the same as the loading buffer; that is, the buffer that is used to dilute the sample before being loaded into the resin. In an embodiment, prior to step (ii), the multi-modal anion exchange resin is equilibrated with an equilibration buffer comprising about 35 mM or less of calcium ions. In another embodiment, the multi-modal anion exchange resin is equilibrated with an equilibration buffer comprising about 20 mM or less of calcium ions. In yet another embodiment, the multi-modal anion exchange resin is equilibrated with an equilibration buffer comprising about 20 mM calcium ions.

In an embodiment, the equilibration buffer, the loading buffer, the wash buffer and the elution buffer each comprise the same amount of calcium ions. In another embodiment, the constituents of the equilibration buffer, loading buffer, wash buffer and elution buffer are the same. In a preferred embodiment, the equilibration buffer, loading buffer, wash buffer and elution buffer each comprise 20 mM 2-(N-morpholino) ethanesulfonic acid (MES), 20 mM $CaCl_2$ and 200 mM NaCl, pH 6.0.

In another embodiment, the equilibration buffer, loading buffer and wash buffer each comprise 200 mM NaCl and 5 mM $Ca^{2+}$ and the Elution buffer comprises 300 mM NaCl and 10 mM $Ca^{2+}$. For example, the equilibration buffer, loading buffer and wash buffer each comprise 20 mM MES, 200 mM NaCl and 5 mM $CaCl_2$ and the Elution buffer comprises 20 mM MES, 300 mM NaCl and 10 mM $CaCl_2$.

As herein described, the present inventors have found that the method of the present invention can remove detergent from the solution containing the Factor VII and/or Factor VIIa, whilst reducing the recovery of Factor VII/Factor VIIa protein aggregates and allowing for greater load volumes.

Thus, in an embodiment of the present invention, the diluted solution from step (i) comprises a detergent.

Any type of detergent may be removed from the solution containing Factor VII and/or Factor VIIa, such as polysorbate (Tween) 80, polysorbate (Tween) 20 and Triton X-100. In an embodiment, the detergent is polysorbate 80 (Polyoxyethylene (20) sorbitan monooleate; PS80). In another embodiment, the solution comprises about 1% detergent (v/v). The detergent may be introduced into the solution by any necessary means, such as during a viral inactivation step.

Where a solution comprising Factor VII and/or Factor VIIa is to be used for clinical or veterinary applications (e.g., for administration to a subject with Factor VII), persons skilled in the art will understand that it may be desirable to reduce the level of active virus content (virus titre) and other potential infectious agents (for example prions) in the solution. Methods of reducing the virus titre in a solution will be known to persons skilled in the art. Examples include pasteurization (for example, incubating the solution at 60° C. for 10 hours in the presence of high concentrations of stabilisers such as glycine (e.g. 2.75 M) and sucrose (e.g. 50%) and/or other selected excipients or salts), dry heat treatment, virus filtration (passing the solution through a nano-filter; e.g., 20 nm cutoff) and/or subjecting the solution to treatment with a suitable organic solvent and detergent for a period of time and under conditions to inactivate virus in the solution. Solvent and detergent has been used for over 20 years to inactivate enveloped viruses particularly in plasma-derived products. Thus it may be carried out using various reagents and methods known in the art (see, for example, U.S. Pat. No. 4,540,573 and U.S. Pat. No. 4,764,369 which are hereby incorporated by reference). Suitable solvents include tri-n-butyl phosphate (TnBP) and ether, preferably TnBP (typically at about 1.0%). Suitable detergents include polysorbate (Tween) 80, polysorbate (Tween) 20 and Triton X-100 (typically at about 0.3%). The selection of treatment conditions including solvent and detergent concentrations depend in part on the characteristics of the solution, with less pure solutions generally requiring higher concentrations of reagents and more extreme reaction conditions. A preferred detergent is polysorbate 80 and a particularly preferred combination is polysorbate 80 and TnBP. The feedstock may be stirred with solvent and detergent reagents at a temperature and for a time sufficient to inactivate any enveloped viruses that may be present. For example, the solvent detergent treatment may be carried out for about 4 hours at 25° C. The virus inactivation step may also comprise virus filtration.

In an embodiment, prior to or subsequent to diluting the solution containing Factor VII and/or Factor VIIa in the loading buffer, the solution is subject to a viral inactivation step. In an embodiment, the viral inactivation step comprises treatment with an organic solvent and detergent. In an embodiment, the organic solvent is tri-n-butyl phosphate and the detergent is polysorbate 80. In another embodiment, the viral inactivation step comprises adding detergent to the solution containing Factor VII and/or Factor VIIa to a final concentration of about 1% v/v.

The present inventors have found that reducing the $Ca^{2+}$ concentration in the loading buffer and/or wash buffer can reduce the load on a multi-modal anion exchange resin and thus allow for greater volumes of solution containing Factor VII and/or Factor VIIa to be loaded onto the resin without adversely affected protein recovery. In an embodiment, the loading buffer and/or the wash buffer comprise about 5 mM or less of calcium ions. In another embodiment, the loading buffer and/or the wash buffer comprise about 5 mM calcium ions. In yet another embodiment, the loading buffer comprises about 5 mM or less of calcium ions and the wash buffer comprises no calcium ions. In yet another embodiment, the loading buffer comprises about 5 mM calcium ions and the wash buffer comprises no calcium ions. In yet another embodiment, the loading buffer comprises about 5 mM or less of calcium ions, the wash buffer comprises no calcium ions and the elution buffer comprises about 35 mM or less of calcium ions. In yet another embodiment, the loading buffer comprises about 5 mM or less of calcium ions, the wash buffer comprises no calcium ions and the elution buffer comprises about 20 mM or less of calcium ions. In yet another embodiment, the loading buffer comprises about 5 mM or less of calcium ions, the wash buffer comprises no calcium ions and the elution buffer comprises about 20 mM calcium ions. In yet another embodiment, the loading buffer comprises about 5 mM calcium ions, the wash buffer comprises no calcium ions and the elution buffer comprises about 20 mM calcium ions.

The ability to load greater volumes of solution containing Factor VII and/or Factor VIIa onto the multi-modal anion exchange chromatographic resin without adversely affected protein recovery in particularly evident in the presence of detergent. In an embodiment, the solution containing Factor VII and/or Factor VIIa to which the detergent has been added is added to the multi-modal anion exchange resin in an amount ranging from about 2 mg to about 30 mg of detergent per mL of resin, preferably from about 4 mg to about 30 mg of detergent per mL of resin. In another embodiment, the solution containing Factor VII and/or Factor VIIa to which the detergent has been added is added to the multi-modal anion exchange resin in an amount ranging from about 6 mg to about 26 mg of detergent per mL of resin. In another embodiment, the solution containing Factor VII and/or Factor VIIa to which the detergent has been added is added to the multi-modal anion exchange resin in an amount of about 16.8 mg of detergent per mL of resin.

The method of the present invention may employ additional purification steps to further purify the Factor VII and/or Factor VIIa containing solution. In an embodiment, the additional purification steps employ additional chromatographic protein purification steps, introduced before and/or after purifying the solution containing Factor VII and/or Factor VIIa through a multi-modal anion exchange resin in accordance with the present invention. The additional chromatographic purification steps may include the use of anion exchange resins, cation exchange resins, hydrophobic charge induction resins, hydrophobic interaction resins or any combination thereof.

In a preferred embodiment, the method further comprises:
(i) passing the Factor VII and/or Factor VIIa that is recovered from the multi-modal anion exchange resin through an anion exchange chromatographic resin under conditions selected such that Factor VII and/or Factor VIIa is bound to the resin;
(ii) washing the resin with a wash solution under conditions selected such that Factor VII and/or Factor VIIa remains bound to the resin;
(iii) eluting the Factor VII and/or Factor VIIa from the resin; and
(iv) recovering the eluted Factor VII and/or Factor VIIa.

In yet another embodiment, the method further comprises, prior to adding the solution to the multi-modal anion exchange resin:
(i) passing the solution containing Factor VII and/or Factor VIIa through an anion exchange chromatographic resin under conditions selected such that Factor VII and/or Factor VIIa is bound to the resin;
(ii) washing the resin with a wash solution under conditions selected such that Factor VII and/or Factor VIIa remains bound to the resin;
(iii) eluting the Factor VII and/or Factor VIIa from the resin; and
(iv) recovering the eluted Factor VII and/or Factor VIIa.

In anion exchange chromatography, negatively charged molecules are attracted to a positively charged solid support. A positively charged solid support can be prepared by any means known to persons skilled in the art and will usually involve the covalent attachment of a negatively charged functional ligand onto a solid support. Suitable negatively charged functional ligands will invariably depend on the molecule to be separated from solution. Examples of suitable anion exchange resins are ones comprising a functional quaternary amine group (Q) and/or a tertiary amine group (DEAE), or a diethylaminopropyl group (ANX). In an embodiment disclosed herein, the anion exchange resin is a strong anion exchange resin. In another embodiment disclosed herein, the strong anion exchange resin comprises a quaternary amine functional ligand (e.g., $-N^+(CH_3)_3$ as seen, for example, in Macroprep-HQ™; Bio-Rad Laboratories). In yet another embodiment the anion exchange resin is trimethylamine groups grafted to a hydroxylated methacrylic polymer via a linking group such as GigaCap Q-650M®.

Other examples of suitable anion exchange resins include Fractogel® EMD TMAE (Trimethylammoniumethyl) on methacrylate polymer resin, Merck; Fractogel® EMD DMAE (dimethylaminoethyl) on methacrylate polymer resin, Merck; POROS 50HQ (quaternary polyethyleneimine) on polystyrenedivinylbenzene particles, Applied Biosystems®; Capto Q (quaternary amine) on cross-linked agarose with dextran surface extender, GE.

In an embodiment, anion exchange chromatography is performed in positive mode with respect to the Factor VII and/or Factor VIIa. That is, the conditions used are such that, when the solution containing Factor VII and/or Factor VIIa is passed through the anion exchange chromatographic resin, the Factor VII and/or Factor VIIa bind(s) to the positively-charged functional groups attached to the resin, allowing impurities in the solution to pass through the resin in the flow-through (drop-through) fraction, where they can be discarded or recovered for other purposes. Once the flow-through fraction passes through the resin, the anion exchange chromatographic resin can be washed with a suitable wash buffer known to persons skilled in the art. The constituents of the wash buffer and the conditions of the wash step will typically be selected to retain the Factor VII and/or Factor bound to the resin during the wash step. The Factor VII and/or Factor VIIa can then be eluted from the resin using suitable buffers known to persons skilled in the art.

Persons skilled in the art will understand that the number of additional chromatographic steps used in accordance with the present invention will depend on the level of purity required in the final preparation. For example, the method of the present invention may comprise 2, 3, 4 or 5 chromatography steps, as disclosed herein. For example, where the method comprises 2 chromatography steps, the sequence of steps will be MM-IEX/IEX or IEX/MM-IEX; where the method comprises 3 chromatography steps, the sequence of steps will be IEX/MM-IEX/IEX or IEX/MM-IEX/MM-IEX or IEX/IEX/MM-IEX or MM-IEX/MM-IEX/IEX; and so forth (where "IEX" denotes ion exchange chromatography and "MM-IEX" denotes multi-modal anion exchange chromatography). The required level of purity may be dictated by the intended use of the solution (e.g., for treatment of patient with a Factor VII deficiency).

In another aspect of the present invention, there is provided a solution comprising Factor VII and/or Factor VIIa recovered by the method according to the present invention, as herein described.

The % recovery of Factor VII and/or Factor VIIa can vary, although the recovery is relatively high. For example, at least 60%, at least 70%, at least 80%, at least 85%, at least 90%, at least 95%, at least 98% or 100% of the Factor VII and/or Factor VIIa present in the starting solution is recovered from the multi-modal anion exchange resin in accordance with the methods of the present invention.

In an embodiment, the solution comprises at least 80% total protein of Factor VIIa.

In another embodiment, the Factor VIIa comprises less than about 1% of aggregated Factor VIIa, preferably less than about 0.8% of aggregated Factor VIIa.

In an embodiment, the solution comprises about 15% total protein or less Factor VII, preferably about 10% total protein of Factor VII.

In another aspect of the present invention, there is provided a solution comprising:
(i) at least about 80% total protein of Factor VIIa; and
(ii) less than about 1% total Factor VIIa in aggregated form.

In another aspect of the present invention, there is provided a solution comprising:
(i) at least about 85% total protein of Factor VIIa; and
(ii) less than about 0.8% total Factor VIIa in aggregated form.

In an embodiment, the solution comprises about 15% total protein or less of Factor VII, preferably about 10% total protein of Factor VII.

In another aspect of the present invention, there is provided a pharmaceutical formulation comprising the solution of the present invention, as herein described, and a pharmaceutically acceptable carrier. Suitable pharmaceutically acceptable carriers, including pharmaceutically acceptable diluents and/or excipients, will be known to those skilled in the art. Examples include solvents, dispersion media, antifungal and antibacterial agents, surfactants, isotonic and absorption agents and the like.

The pharmaceutical formulation may also be formulated by the addition of a combination of suitable stabilisers, for example, an amino acid, a carbohydrate, a salt, and a detergent. In particular embodiments, the stabiliser comprises a mixture of a sugar alcohol and an amino acid. The stabilizer may comprise a mixture of a sugar (e.g. sucrose or trehalose), a sugar alcohol (e.g. mannitol or sorbitol), and an amino acid (e.g. proline, glycine and arginine). The pharmaceutical formulation may also be sterilised by filtration prior to dispensing and long term storage. Preferably, the formulation will retain substantially its original stability characteristics for at least 2, 4, 6, 8, 10, 12, 18, 24, 36 or more months. For example, formulations stored at 2-8° C. or 25° C. can typically retain substantially the same molecular size distribution as measured by HPLC-SEC when stored for 6 months or longer. Particular embodiments of the pharmaceutical formulation can be stable and suitable for commercial pharmaceutical use for at least 6 months, 12 months, 18 months, 24 months, 36 months or even longer when stored at 2-8° C. and/or room temperature.

The solutions and pharmaceutical formulations of the present invention, as herein described, may be formulated into any of many possible dosage forms, such as injectable formulations. The formulations and their subsequent administration (dosing) are within the skill of those in the art. Dosing is dependent on the responsiveness of the subject to treatment, but will invariably last for as long as the desirable effect is required (e.g., a return to normal plasma levels of Factor VII). Persons of ordinary skill can easily determine optimum dosages, dosing methodologies and repetition rates.

In another aspect of the present invention, there is provided a method of treating or preventing a condition associated with Factor VII deficiency, the method comprising administering to a subject in need thereof the solution or pharmaceutical formulation of the present invention, as herein described. The type of conditions that can be targeted for treatment in accordance with the present invention would be known to persons skilled in the art. In an embodiment, the condition is selected from the group consisting of excessive bleeding and excessive bruising.

In another aspect of the present invention, there is provided a use of the solution according to the present invention, as herein described, in the manufacture of a medicament for treating or preventing a condition associated with Factor VII deficiency.

Whilst the methods of the present invention can be performed at laboratory scale, they can be scalable up to industrial size without significant changes to conditions. Thus, in an embodiment disclosed herein, the methods of the present invention are performed on an industrial or commercial scale. Preferably, the methods of the invention are suitable for the commercial scale purification of Factor VII and/or Factor VIIa. For example, a commercial scale process may involve the use of a Factor VII and/or Factor VIIa-containing solution with a volume in the range from about 2,000 to about 20,000 liters.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1

Purification of Recombinant Activated Factor VIIa Fusion Protein (rVIIa-FP) Using Mixed-Mode Anion Exchange Chromatographic Resin (Capto™ Adhere)

Figure 5:
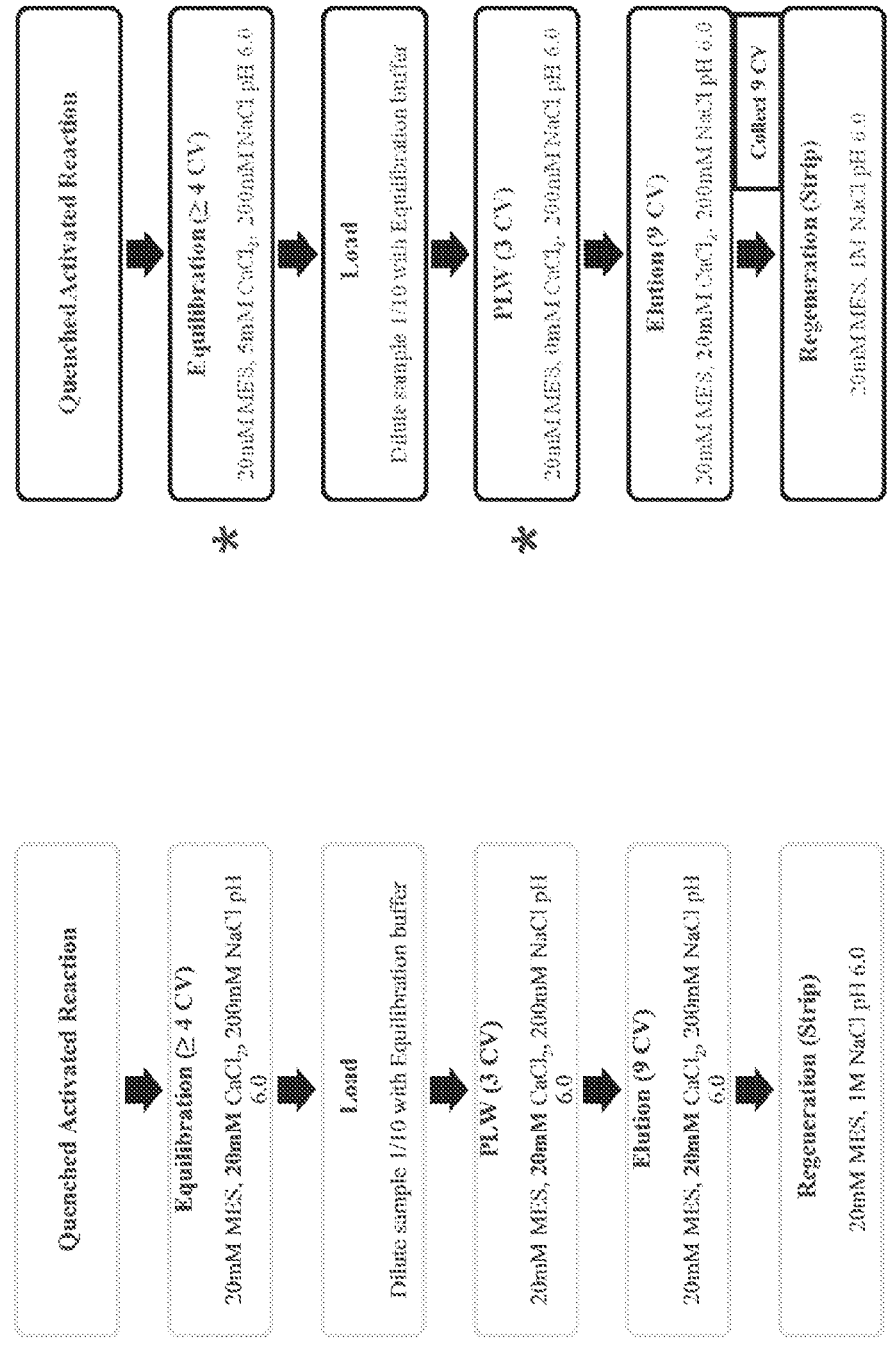
FIG. 5 shows a flow diagram of the purification of Factor VIIa through a multi-mode anion exchange resin (Capto™ Adhere) using two different purification processes that differ in the amount of Ca$^{2+}$ present in the equilibration, load (dilution), PLW and Elution buffers.

In this example, rVIIa-FP (rVIIa-FP meaning an albumin fused FVIIa with a linker length of 31 amino acids as described in WO 2007/090584) purification is a multi-step process in which the Capto™ Adhere is included. The Capto™ Adhere (anion exchange/hydrophobic mixed mode resin) column targets the clearance of detergent (polysorbate 80; Polyoxyethylene (20) sorbitan monooleate; PS80) and solvent (tri-n-butyl phosphate; TnBP) present in the solution containing rVIIa-FP. In this example, the solution containing rVIIa-FP was eluted from an anion exchange chromatographic resin and PS80 was introduced into the solution during a viral inactivation step and was present at a final concentration of approximately 1% v/v. In this example, the Capto™ Adhere column operates in a 'pseudo-flow through (FT)' mode, namely because the Load/Equilibration buffer (20 mM 2-(N-morpholino)ethanesulfonic acid (MES), 20 mM $CaCl_2$, 200 mM NaCl, pH 6.0) is identical to the Post-Load Wash (PLW) and Elution buffers. This is further illustrated in FIG. 5 (left flow chart). However, the present inventors found that the effectiveness of the purification was restricted by a low PS80 capacity, with an apparent breakthrough occurring at >4.1 mg PS80/ml resin (FIG. 1). As such, resin capacity is dictated by the total volume of the load. Without being bound by theory, the inventors suspect that PS80 partially binds to the Capto™ Adhere resin (through hydrophobic interactions) and experiences overloading when its threshold is reached. As a result, at high PS80 load conditions, separation of UV absorbance (A280) between the PLW and the Elution fractions within the purification method is impeded, such that a clear signal for collection of the Eluate fraction (comprising rVIIa-FP) is in doubt. This can lead to a reduction in protein recovery. With this in mind, the inventors sought to (i) to increase the load capacity of the volume loaded onto the Capto™ Adhere resin and thereby reduce the cost of the Capto™ Adhere purification step.

The present inventors found that the safe operating range for the Capto™ Adhere was <3.6 mg PS80/ml resin. A load value>4.1 mg PS80/ml resin resulted in an unclear separation between the absorbencies of the PLW and that of the Elution fractions (FIG. 1). An apparent PS80 breakthrough was observed in the flow through (FT) and the PLW/Elution fractions. This observation lead to the exploration of new buffer conditions to improve the current rVIIa-FP purification step on the Capto™ Adhere.

Example 2

Purification of rVIIa-FP Using Capto™ Adhere—Reduction in $Ca^{2+}$

Figure 2:
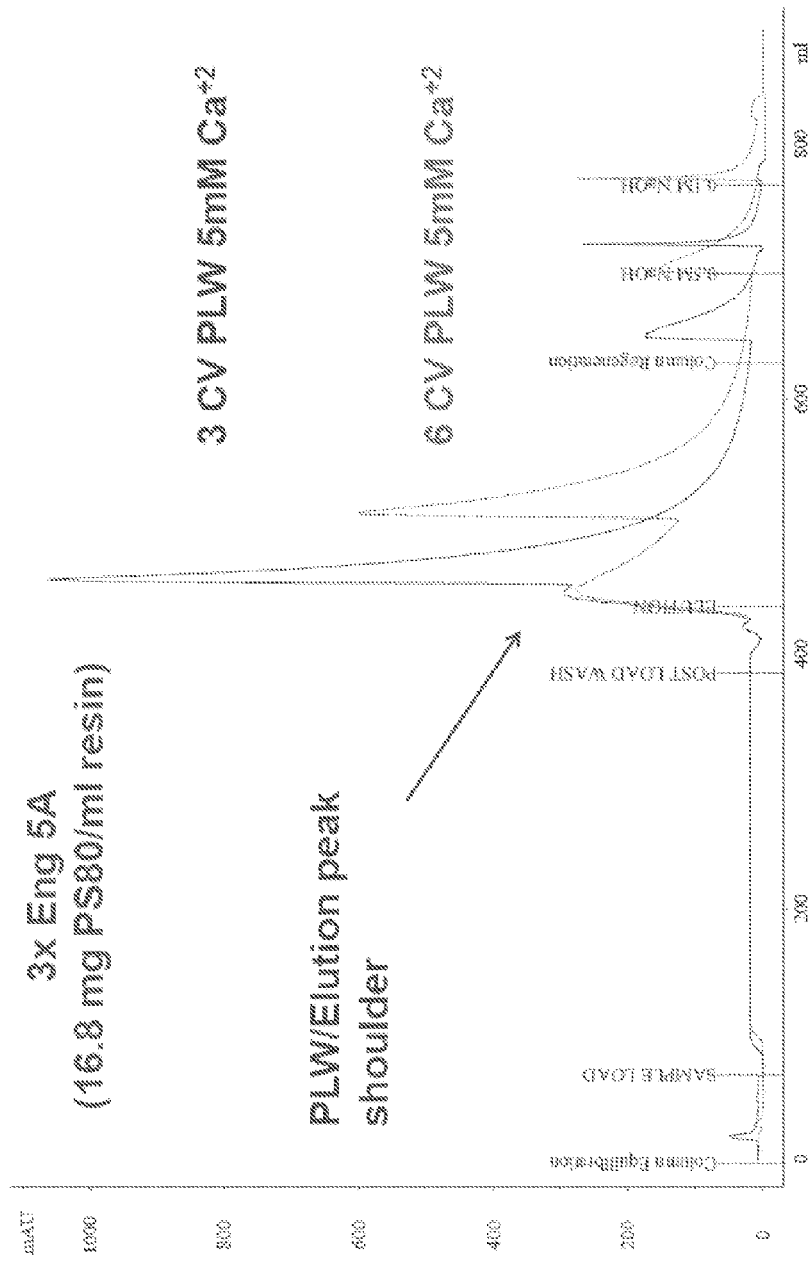
FIG. 2 shows an overlay of Akta chromatograms using different volume of PLW buffer. 3CV PLW (highest peak at appr. 475 min). 6CV PLW (highest peak at appr. 525 min). Load and Equilibration/PLW buffer containing 5 mM $CaCl_2$. Total PS80 was 16.8 mg/ml resin (3×Eng 5A level).

In this example, the inventors reduced the concentration of $Ca^{2+}$ ($CaCl_2$) in the Equilibration, Dilution (Load) and PLW. This change resulted in no apparent breakthrough in the FT fraction (FIG. 2), although a slight "shoulder" on the Elution peak was observed in the PLW/Elution fraction (FIG. 2, 3CV (column volume) PLW). Whilst a 6CV PLW was implemented to wash the shoulder from the Elution peak, this lead to the slight loss of protein recovery. These results indicate that 5 mM $Ca^{2+}$ in the Equilibration/Load/PLW/buffers increases total load capacity onto the column, although the inclusion of 5 mM $CaCl_2$ in the PLW buffer can result in some loss of protein from the Capto™ Adhere column.

Example 3

Purification of rVIIa-FP Using Capto™ Adhere—No $Ca^{2+}$

Figure 3:
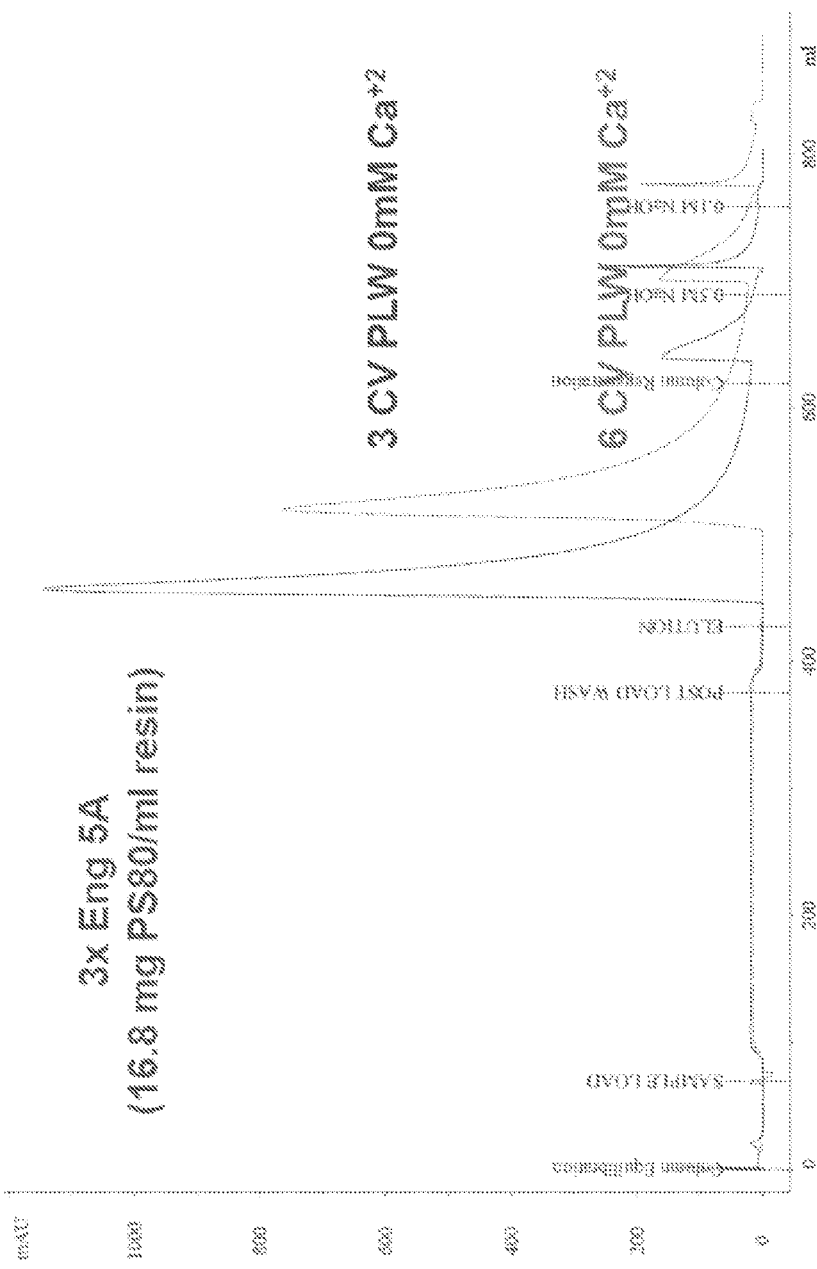
FIG. 3 shows an overlay of Akta chromatograms using different volume of PLW buffer containing no calcium. 3CV PLW (highest peak at appr. 475 min). 6CV PLW (highest peak at appr. 525 min). Load and Equilibration buffer containing 5 mM $CaCl_2$ with no calcium in the PLW buffer. Total PS80 was 16.8 mg/ml resin (3×Eng 5A level).

To address the loss of protein from the Capto Adhere column at low $Ca^{2+}$ concentrations, a PLW containing no calcium was investigated. When this PLW buffer was used, a single Elution peak was observed in the 3CV and 6CV PLW conditions. No apparent breakthrough was observed in the FT and PLW fractions (FIG. 3). The inventors also found that there was no difference in the recovery of activity and protein and in the RP-HPLC profile between the test conditions (Examples 2 and 3) and the Control conditions (Example 1; 20 mM $CaCl_2$). Furthermore, the altered load and wash conditions did not adversely affect the clearance of PS80 across this step.

Example 4

Purification of rVIIa-FP Using Capto™ Adhere—Load Capacity

Figure 4:
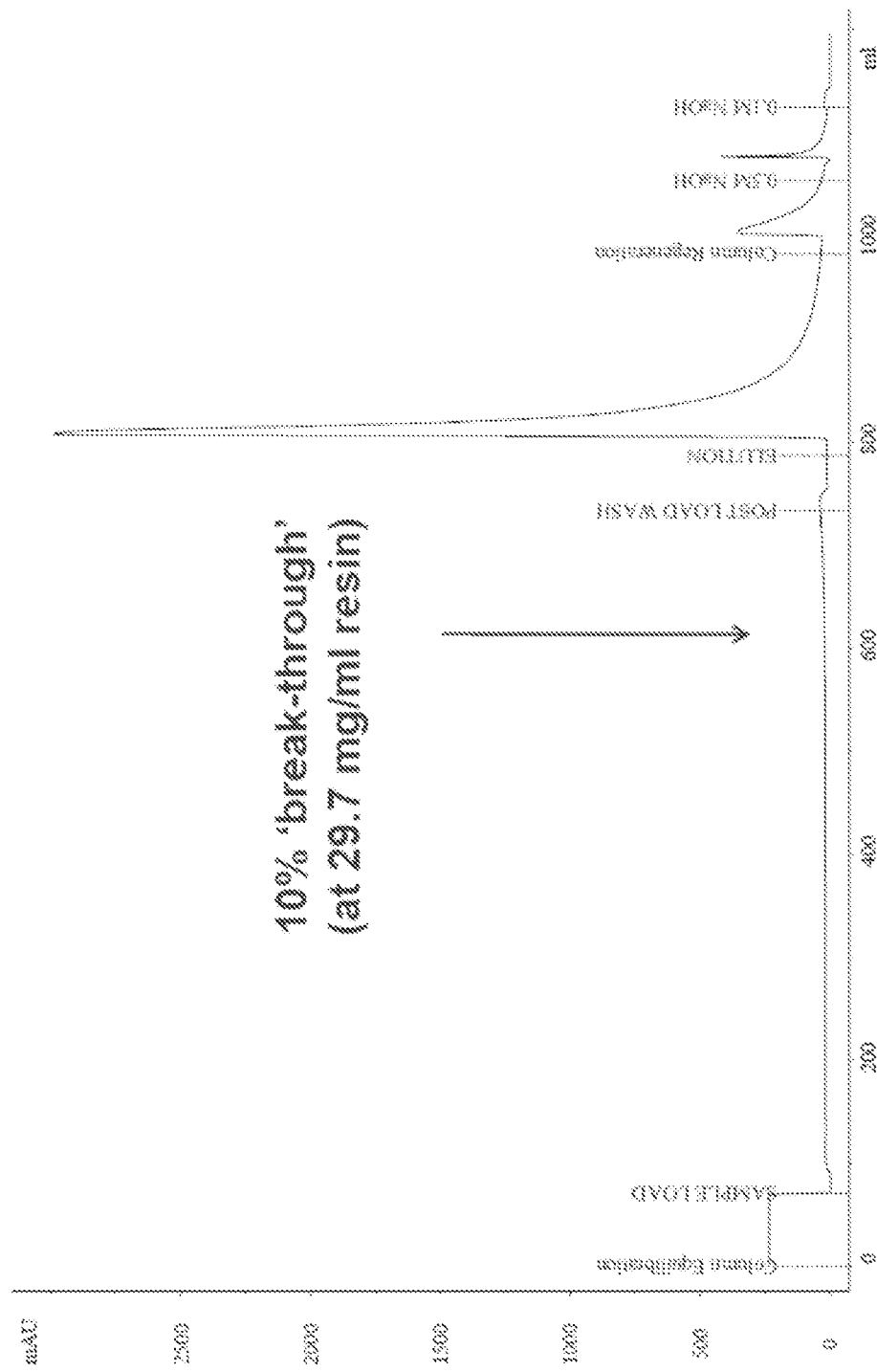
FIG. 4 shows a chromatogram of the determination of load capacity for 5 mM CaCl$_2$ under conditions determined from FIG. 4 (using 3CV PLW).

As shown in FIG. 4, apparent breakthrough of PS80 (at 10% OD increase) was observed at 29.7 mg PS80/ml resin (5.3×Eng 5A level). Resin lot-to-lot variation has been observed for the Capto Adhere resin when challenged with the Capto Load (3 resins tested). In one example, apparent PS80 breakthrough was observed at 25.2 mg PS80/ml resin (4.5×Eng 5A level). Based on this, an interim maximum load capacity of 16.8 mg PS80/ml resin has been established (3×Eng 5A level). Table 1 shows the Results Summary of data generated from Example 1 to 4, above. The table indicates that reducing calcium to 5 mM in the Load/Equilibration buffer(s) and to no calcium in the PLW buffer does not substantially affect product quality across this column when compared to that of the Control run (i.e., using 20 mM $CaCl_2$). Activity and protein recovery, aggregate content and VIIa content was not affected by the changed load, equilibration and PLW buffer conditions.

Similar experiments were undertaken to compare control conditions using 20 mM $Ca^{2+}$ in the Equilibration/Load/PLW/Elution buffers ("DEV" and "Eng5A") with a test run using 5 mM $Ca^{2+}$ in the Equilibration/Load buffer, no $Ca^{2+}$ in the PLW buffer and 20 mM $Ca^{2+}$ in the Elution buffer ("New Method"). As summarised in FIG. 6, reducing the $Ca^{2+}$ in the Equilibration/Load buffer and having no $Ca^{2+}$ in the PLW buffer did not adversely affect recovered protein activity (Eluate), as determined by the Staclot method, although it did appear to improve protein recovery as determined by chromogenic and UV determination. Reducing the $Ca^{2+}$ in the Equilibration/Load buffer and having no $Ca^{2+}$ in the PLW buffer also reduced the amount of recovered protein in aggregate form (in the eluate), as determined by SE-HPLC. Also of importance is that reducing the $Ca^{2+}$ in the Equilibration/Load buffer and having no $Ca^{2+}$ in the PLW buffer increased load capacity of the Capto™ Adhere resin while not affecting PS80 clearance (FIG. 6).

TABLE 1

Summary of analysis of Capto ™ Adhere Eluates in the current and new buffer conditions:

| Buffer Conditions | Load PS80 (mg/ml resin) | Chromogenic Recovery (%) | Staclot Recovery (%) | Protein Recovery (%) | Aggregates (%) | VIIa (%) | HCP Clearance (x fold) | Eluate PS80 (%) |
|---|---|---|---|---|---|---|---|---|
| 20 mM $CaCl_2$ (Dilution/ PLW/Elution) | 5.6 | 70 | 72 | 64 | 3.4 | 88 | 4 | 0.002 |

TABLE 1-continued

Summary of analysis of Capto ™ Adhere Eluates in the current and new buffer conditions:

| Buffer Conditions | Load PS80 (mg/ml resin) | Chromo-genic Recovery (%) | Staclot Recovery (%) | Protein Recovery (%) | Aggregates (%) | VIIa (%) | HCP Clearance (x fold) | Eluate PS80 (%) |
|---|---|---|---|---|---|---|---|---|
| 5 mM/5 mM/ 20 mM CaCl$_2$ 2 (Dilution/ PLW/Elution) | 16.8 | 81 | 86 | 75 | 0.7 | 87 | ND | 0.002 |
| 5 mM/0 mM/ 20 mM CaCl$_2$ (Dilution/ PLW/Elution) | 16.8 | 95 | 73 | 80 | 0.7 | 86 | 8 | 0.001 |
| 5 mM/0 mM/ 20 mM CaCl$_2$ (Dilution/ PLW/Elution) | 39.2 | 101 | 98 | 69 | 1.3 | 89 | 7 | 0.004 |

From these examples, the load capacity of the Capto™ Adhere can be increased 4.7-fold over the current load levels (i.e., from <3.6 mg PS80/ml resin to 16.8 mg PS80/ml resin). As shown with the current operating process, the majority of the PS80 was removed by Capto™ Adhere resin in the FT fraction. This value was not altered by the new elution conditions. With the implementation of the reduced calcium conditions for the Capto™ Adhere column, the mode of the operation of the column has changed from a 'pseudo-FT' to that of a "bind and elute" method of purification, allowing for greater control over the chromatographic purification process.

Example 5

Figure 7:
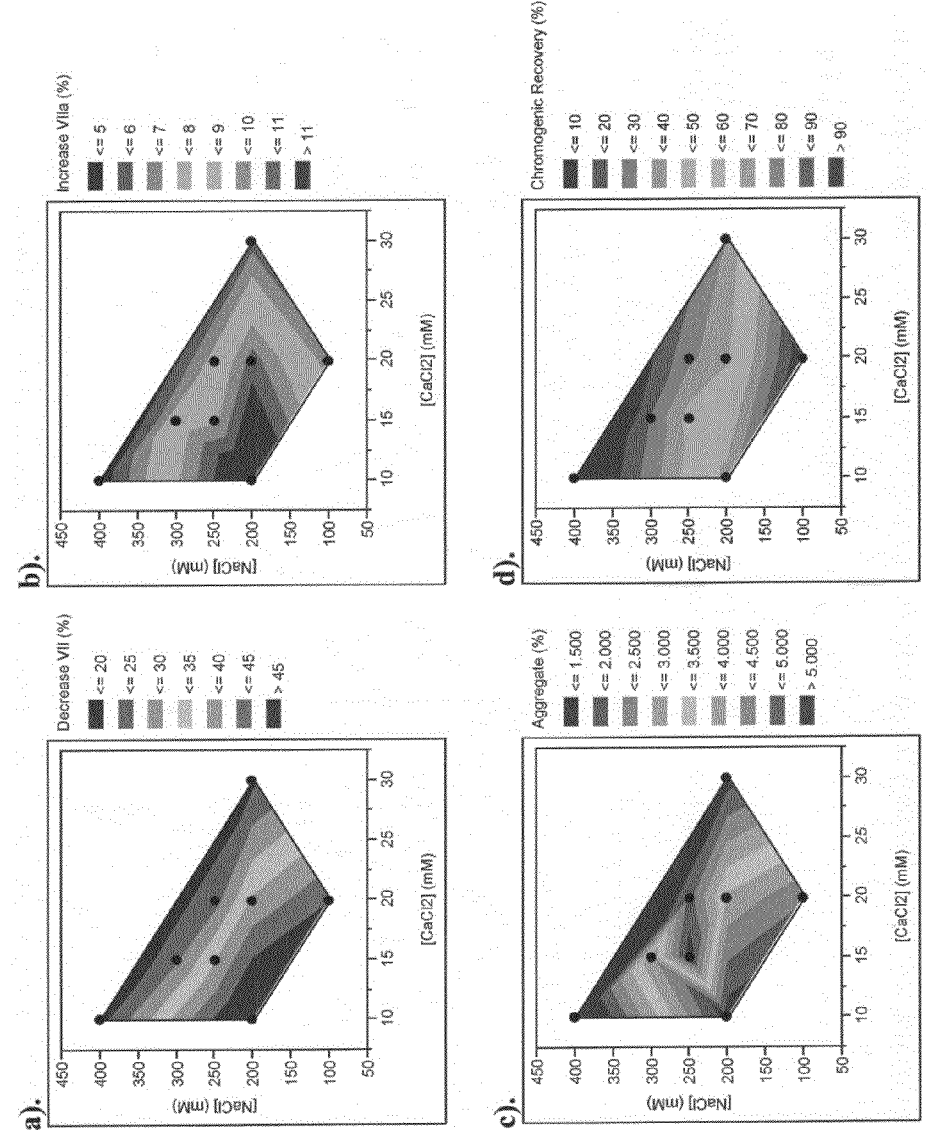
FIG. 7 shows contour plots demonstrating the dependence of an increase in Factor VIIa-fusion protein (rVIIa-FP) (a), recovery (%) (b), decrease in rVII-FP (c) and aggregate content (%) (d) with NaCl and CaCl$_2$ concentrations in the Capto™ Adhere eluate compared to that of the diluted load. The load material was diluted 1:10 with Equilibration/PWL/Elution buffer for each trial condition.

Dependence of an Increase in Recombinant Factor VIIa Fusion Protein (rVIIa-FP), Recovery (%), Decrease in rVIIa-FP and Aggregate Content (%) on NaCl and CaCl$_2$ Levels The inventors sought to determine optimal Ca$^{2+}$ and NaCl concentrations in the Equilibration/Load buffers for recombinant Factor VII and Factor VIIa. FIG. 7 shows contour plots demonstrating the dependence of an increase in recombinant Factor VIIa-fusion protein (rVIIa-FP) (a), recovery (%) (b), decrease in rVII-FP (c) and aggregate content (%) (d) with NaCl and CaCl$_2$ concentrations in the Capto™ Adhere eluate, compared to that of the diluted load. The load material was diluted 1:10 with Equilibration/PWL/Elution buffer for each trial condition. Data from FIG. 7 were selected and included in Table 2, below. In this experiment, the optimal conditions for Factor VIIa recovery and minimal aggregate recovery was 200 mM NaCl and 20 mM calcium for the Eluate buffers (circled)

TABLE 2

Capto ™ Adhere CaCl$_2$ and NaCl optimization

| [Calcium] (mM) | [NaCl] (mM) | VIIa[1] (%) | VII[2] (%) | Aggregate (%) | Recovery[3] (%) |
|---|---|---|---|---|---|
| 10 | 200 | 11.4 | 45.3 | 1.2 | 36 |
| 10 | 400 | 4.3 | 82.1 | 6.2 | 114 |
| 20 | 100 | 6.4 | 44.6 | 2.1 | 0.2 |
| 30 | 200 | 5.5 | 18.5 | 5.3 | 70 |
| 20[4] | 200 | 11.2 | 35.6 | 2.4 | 70 |

[1], Percentage (%) increase of VIIa in the Eluate compared to that of the Diluted Load
[2], Percentage (%) decrease of VII in the Eluate compared to that of the Diluted Load
[3], Chromogenic Recovery (%)
[4], Optimal condition The inventors sought to further determine optimal Ca$^{2+}$ and NaCl concentrations in the Equilibration/Load buffers for recombinant Factor VII and Factor VIIa recovery using a 96-well High Through-Put platform. The Load material was a solution comprising recombinant Factor VIIa, loaded onto Capto™ Adhere resin (20 μL resin per well).

Different Equilibration buffer components were screened, as shown in Table 3. The sample containing recombinant Factor VII and/or Factor VIIa was diluted in the appropriate Equilibration buffer at a 1:20 ratio prior to loading onto the resin. In this experiment, the diluted solution comprised 0.1% PS80/0.03% TnBP.

Results in Table 3 show the ratio of total absorbance in the Eluate divided by the total absorbance in the flow-through. That is, Eluate OD divided by flow-through OD. Higher ratios suggests that protein binding to resin was high and loss during loading was low. In this experiment, the favoured condition was 200 mM NaCl and 5 mM calcium for the Load/Equilibration/PLW buffers.

Different Elution buffer components were also screened, as shown in Table 4. The results show the reversed phase (RP)-HPLC data of the Eluate as a percentage of peak area. Optimal conditions were determined to maximise VIIa content while minimising degradation and reducing VII content. In this particular high through-put experiment, the favoured condition was 300 mM NaCl and 10 mM calcium for the Elution buffer. This condition resulted in 85.5% VIIa, 10.8% VII and 3.7% Degradation (SP).

Figure 8:
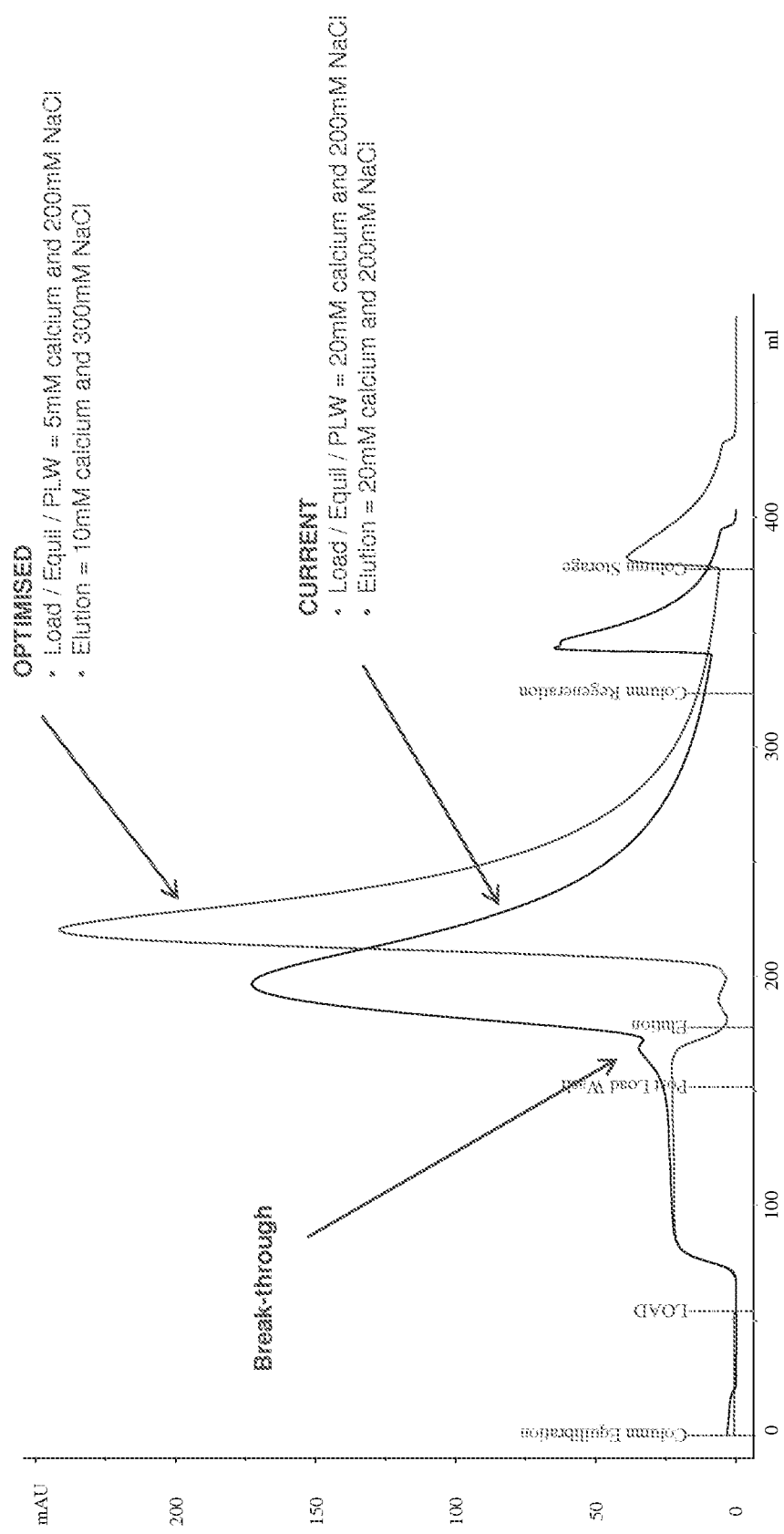
FIG. 8 shows an overlay of Akta chromatograms using the further optimised NaCl and CaCl$_2$ conditions in the Equilibration/Load/PLW buffers and the Elution buffer, as compared to the use of 200 mM NaCl and 20 mM CaCl$_2$ in each of the Equilibration/Load/PLW and Elution buffers.

When the favourable conditions were applied for the purification of recombinant Factor VII/Factor VIIa in a small-scale trial (i.e., 200 mM NaCl and 5 mM calcium in the Load/Equilibration/PLW buffers and 300 mM NaCl and 10 mM calcium for the Elution buffer), there was a further improvement in the separation of peaks and protein recovery as compared to the use of 200 mM NaCl and 20 mM calcium in the Equilibration/Load/PLW/Eluate buffers, as shown in the overlay of Akta chromatograms (FIG. 8). Data derived from FIG. 8 are provided in Table 5. The data for "pseudo-FT/current method" were derived from the use of 200 mM NaCl and 20 mM calcium in the Equilibration/Load/PLW/Eluate buffers, whereas the data for "bind and elute/HTP Optimized" were derived from the use of (i) 200 mM NaCl and 5 mM calcium for the Load/Equilibration/PLW buffers and (ii) 300 mM NaCl and 10 mM calcium in the Elution buffer. The data from Table 5 demonstrate that the change of NaCl and $CaCl_2$ conditions in this instance improved Factor VIIa recovery without adversely affecting aggregate recovery in the eluate.

TABLE 3

Load/Equilibration/PWL buffer optimization
Ratio

| NaCl mM | Calcium mM | | | | | | | |
|---|---|---|---|---|---|---|---|---|
|  | 0 | 1.25 | 2.5 | 5 | 7.5 | 10 | 20 | 30 |
| 50 | 1.287 | 1.385 | 1.165 | 1.098 | 1.455 | 1.404 | 1.225 | 1.306 |
| 100 | 1.237 | 1.365 | 1.308 | 1.547 | 1.523 | 1.563 | 1.334 | 0.979 |
| 200 | 1.764 | 1.678 | 1.640 | 1.996 | 1.608 | 1.195 | 0.750 | 0.512 |

The invention claimed is:

1. A method of purifying Factor VII and/or Factor VIIa from a solution containing either or both proteins, the method comprising:
   (i) diluting the solution containing recombinant Factor VII and/or Factor VIIa in a loading buffer;
   (ii) adding the diluted solution from step (i) to a multi-modal anion exchange resin under conditions selected such that recombinant Factor VII and/or Factor VIIa is bound to the resin;
   (iii) adding an elution buffer to the resin under conditions selected such that recombinant Factor VII and/or Factor VIIa is eluted from the resin; and
   (iv) recovering the eluted recombinant Factor VII and/or Factor VIIa; wherein the loading buffer comprises 5 mM or less of calcium ions.

2. The method of claim 1, further comprising washing the resin after step (ii) with a wash buffer under conditions such that Factor VII and/or Factor VIIa remains bound to the resin, wherein the wash buffer comprises 5 mM or less of calcium ions.

3. The method of claim 2, wherein the loading buffer comprises 5 mM or less of calcium ions and the wash buffer comprises no calcium ions.

TABLE 4

Elution buffer optimization

| % Area | $CaCl_2$ (mM) | | | | | | | | | | | | | | |
|---|---|---|---|---|---|---|---|---|---|---|---|---|---|---|---|
| NaCl(mM) | 5(L) | 5(D) | 5(F) | 5(H) | 5(L + H) | 10(L) | 10(D) | 10(F) | 10(H) | 10(L + H) | 20(L) | 20(D) | 20(F) | 20(H) | 20(L + H) |
| 200 | 14.2 | 3.4 | 12.1 | 70.3 | 84.5 | 14.0 | 3.8 | 11.9 | 70.3 | 84.3 | 13.6 | 3.9 | 11.7 | 70.8 | 84.4 |
| 300 | 14.1 | 3.7 | 11.3 | 70.8 | 85.0 | 13.9 | 3.7 | 10.8 | 71.6 | 85.5 | 13.7 | 3.8 | 11.4 | 71.1 | 84.8 |
| 400 | 13.2 | 3.9 | 11.1 | 71.9 | 85.0 | 13.9 | 3.9 | 12.2 | 70.1 | 83.9 | 13.5 | 3.9 | 11.5 | 71.1 | 84.6 |
| 500 | 12.3 | 4.0 | 11.7 | 71.9 | 84.3 | 13.5 | 4.0 | 11.8 | 70.7 | 84.1 | 13.5 | 3.9 | 11.9 | 70.8 | 84.3 |

| % Area | $CaCl_2$ (mM) | | | | | | | | | | | | | | |
|---|---|---|---|---|---|---|---|---|---|---|---|---|---|---|---|
| NaCl(mM) | 30(L) | 30(D) | 30(F) | 30(H) | 30(L + H) | 40(L) | 40(D) | 40(F) | 40(H) | 40(L + H) | 50(L) | 50(D) | 50(F) | 50(H) | 50(L + H) |
| 200 | 13.5 | 3.9 | 11.3 | 71.4 | 84.8 | 13.8 | 4.1 | 11.7 | 70.4 | 84.2 | 13.4 | 4.1 | 12.0 | 70.5 | 83.9 |
| 300 | 13.9 | 3.9 | 11.4 | 70.8 | 84.7 | 12.2 | 4.2 | 11.9 | 71.7 | 84.0 | 13.1 | 4.3 | 12.3 | 70.3 | 83.4 |
| 400 | 13.2 | 3.9 | 11.5 | 71.4 | 84.6 | 13.7 | 4.2 | 12.1 | 70.1 | 83.7 | 12.6 | 4.3 | 11.7 | 71.3 | 84.0 |
| 500 | 11.2 | 4.2 | 12.0 | 72.6 | 83.8 | 13.5 | 4.0 | 12.3 | 70.3 | 83.7 | 13.1 | 4.2 | 11.4 | 71.3 | 84.4 |

L = Factor VIIa light chain; D = Factor VIIa degradation product (SP); F = full length Factor VII (non-activated); H = Factor VIIa heavy chain; (L + H) = combined Factor VIIa light and heavy chain values

TABLE 5

Comparison of Small-"scale pseudo"-FT Capto Adhere to HTP
Optimised Bind and Elute Capto Adhere to Chromatography

| Column Operation | | Recovery (%) | | | RP-HPLC (%) | | | SE-HPLC (%) | |
|---|---|---|---|---|---|---|---|---|---|
| Mode | Step | Chromogenic | Staclot | Protein | VIIa | VII | SP | Aggregate | Monomer |
| "pseudo" FT (current method) | Load |  |  |  | 78.9 | 9.2 | 3.6 | 7.3 | 92.5 |
|  | FT |  | 4 | 2 |  |  |  |  |  |
|  | Eluate | 86 | 86 | 77 | 78.9 | 7.7 | 3.6 | 0.5 | 98.4 |
|  | Strip |  | 6 | 10 |  |  |  |  |  |
| Bind and Elute (HTP Optimised) | Load |  |  |  | 78.7 | 9.8 | 3.7 | 8.1 | 91 |
|  | FT |  | ND | 1 |  |  |  |  |  |
|  | Eluate | 91 | 90 | 83 | 79.3 | 7.7 | 3.7 | 0.7 | 98.2 |
|  | Strip | NA | 5 | 8 |  |  |  |  |  |

Note:
1. ND = Not Detected.
2. Cells left blank where not assayed for results

4. The method of claim 1, wherein the solution containing recombinant Factor VII and/or Factor VIIa is subjected to a viral inactivation step prior to diluting the solution in the loading buffer.

5. The method of claim 4, wherein the viral inactivation step comprises treatment with an organic solvent and detergent.

6. The method of claim 5, wherein the organic solvent is tri-n-butyl phosphate and the detergent is polysorbate 80.

7. The method of claim 5, wherein the viral inactivation step comprises adding the detergent to the solution containing recombinant Factor VII and/or Factor VIIa to a final concentration of about 1% v/v.

8. The method of claim 7, wherein the solution containing recombinant Factor VII and/or Factor VIIa, and to which the detergent, is added to the multi-modal anion exchange resin in an amount ranging from about 4 mg to about 30 mg of detergent per mL of resin.

9. The method of claim 1, further comprising:
(i) passing the solution containing recombinant Factor VII and/or Factor VIIa through an anion exchange chromatographic resin under conditions selected such that recombinant Factor VII and/or Factor VIIa is bound to the resin;
(ii) washing the resin with a wash solution under conditions selected such that recombinant Factor VII and/or Factor VIIa remains bound to the resin;
(iii) eluting the recombinant Factor VII and/or Factor VIIa from the resin; and
(iv) recovering the eluted recombinant Factor VII and/or Factor VIIa.

10. The method of claim 1, wherein the multi-modal anion exchange resin comprises N-benzyl-n-methyl ethanolamine.

11. The method of claim 1, wherein the loading buffer further comprises about 200 mM sodium chloride or less.

12. The method of claim 2, wherein the loading and wash buffers further comprise about 200 mM sodium chloride.

13. The method of claim 2, wherein the loading buffer, the washing buffer, and the elution buffer further comprise about 20 mM 2-(N-morpholino)ethanesulfonic acid (MES) and about 200 mM NaCl at a pH of about 6.0.

14. The method of claim 1, wherein the elution buffer comprises more than 5 mM calcium ions.

15. The method of claim 1, wherein the elution buffer comprises about 5-35 mM calcium ions.

16. The method of claim 1, wherein the recombinant Factor VII and/or Factor VIIa is fused to albumin.

17. The method of claim 1, wherein the eluted recombinant Factor VII and/or Factor VIIa comprises less than 1% of aggregated Factor VII and/or Factor VIIa.

18. The method of claim 1, wherein the eluted recombinant Factor VII and/or Factor VIIa comprises at least 80% of the total Factor VII and/or Factor VIIa present in the diluted solution of step (i).

* * * * *